United States Patent [19]
Roper et al.

[11] Patent Number: 5,014,713
[45] Date of Patent: May 14, 1991

[54] METHOD AND APPARATUS FOR MEASURING THICKNESS OF FAT USING INFRARED LIGHT

[75] Inventors: Alan Roper, Talent; Keith O. Johnson, Medford, both of Oreg.

[73] Assignee: Tarris Enterprises, Inc., White City, Oreg.

[21] Appl. No.: 446,054

[22] Filed: Dec. 5, 1989

[51] Int. Cl.$^5$ .......................... A61B 5/00; G01N 21/00
[52] U.S. Cl. .................................. 128/664; 128/633; 128/774; 250/341
[58] Field of Search .................. 128/633, 660.02, 664, 128/665, 774; 250/339, 341, 358.1

[56] References Cited

U.S. PATENT DOCUMENTS

| | | |
|---|---|---|
| 3,671,858 | 6/1972 | Knudsen et al. |
| 4,633,087 | 12/1986 | Rosenthal et al. |
| 4,700,708 | 10/1987 | New, Jr. et al. ............ 128/633 |
| 4,785,817 | 11/1988 | Stouffer . |
| 4,801,804 | 1/1989 | Rosenthal . |
| 4,807,631 | 2/1989 | Hersh et al. ............... 128/633 |
| 4,819,752 | 4/1989 | Zelin ........................ 128/633 |
| 4,850,365 | 7/1989 | Rosenthal ................. 128/664 |
| 4,880,304 | 11/1989 | Jaeb et al. ................. 128/633 |
| 4,926,867 | 5/1990 | Kanda et al. .............. 128/633 |
| 4,928,014 | 5/1990 | Rosenthal ................. 128/664 |

FOREIGN PATENT DOCUMENTS

| | | | |
|---|---|---|---|
| 1297782 | 3/1987 | U.S.S.R. ............ 128/660.02 |
| 1308319 | 5/1987 | U.S.S.R. ............ 128/660.02 |

Primary Examiner—Lee S. Cohen
Assistant Examiner—Krista M. Pfaffle
Attorney, Agent, or Firm—Chernoff, Vilhauer, McClung & Stenzel

[57] ABSTRACT

A body fat thickness measuring device comprising a pair of infrared emitting diodes, one emitting a steady, low-intensity light, and the other emitting periodic, high-intensity pulses of light, to be placed against the skin where the fat is to be measured. The device contains an array of detectors in the form of infrared-sensitive photo-transistors which are placed against the skin in predetermined locations near the two diodes, yet shielded from ambient light. The detector array provides signals proportional to the amount of infrared light detected, and these signals are summed and amplified, forming a composite signal. The amplitude of this composite signal, which is indicative of the thickness of the layer of fat, is displayed on a digital readout device.

8 Claims, 2 Drawing Sheets 5,014,713

METHOD AND APPARATUS FOR MEASURING THICKNESS OF FAT USING INFRARED LIGHT

BACKGROUND OF THE INVENTION

The present invention relates to measuring the thickness of body fat. More specifically, the present invention includes a method and apparatus for non-invasively determining body fat thickness using infrared light.

In today's health conscious world, people are becoming aware fitness involves more than maintaining proper body weight as indicated by a bathroom scale. Muscle tissue is heavier, and generally more desirable than fat tissue, but a scale treats their weights the same. It is necessary to determine the amount of body fat to get an accurate indication of total fitness.

Body fat has been measured using many different techniques. By immersing a body in water, its total fat composition can be determined. A simpler technique involves measuring the thickness of fat at various locations on the body using a skinfold caliper. Unfortunately, accurate results with a skinfold caliper require not only consistent operation of the calipers, but also require a second person to take the measurements in locations where the person being measured cannot readily see the caliper reading if attempting to do the measurement on him or herself.

The measurement of fat layer thicknesses is also important to the meat packaging industry, with the result that various methods have been used to measure fat on animals. However, many of the fat measurement techniques used in that industry are invasive and thus inappropriate for fitness measurement purposes. For example, Shigeo Tauchi et al. Japanese laid-open patent application No. 56-160622 describes using colored filters to optically determine the fat thickness for a butchered cross section of meat, and Knudsen et al U.S. Pat. No. 3,671,858 discloses a method of using a needle having electrical contacts to measure electrical resistances between various layers of flesh.

Yoshio Takemori Japanese laid-open application No. 60-181606, Hiroyuki Toyokawa Japanese laid-open application No. 62-156508, and Stouffer U.S. Pat. No. 4,785,817 each disclose a noninvasive method of measuring fat thickness using ultrasonic waves.

SUMMARY OF THE INVENTION

The present invention provides apparatus and means using infrared radiation for quickly, accurately, and noninvasively measuring the thickness of body fat.

In accordance with the present invention, a pair of infrared emitting diodes, one emitting a steady, low-intensity light, and the other emitting periodic, high-intensity pulses of light, are placed against the skin where the fat is to be measured. The low-intensity, steady illumination provides a base infrared level in the fat and reduces the effect of ambient light, while the high-intensity pulses refract through the fat, providing an indication of its thickness. An array of infrared-sensitive photo-transistors are placed against the skin at predetermined locations near the two diodes, yet shielded from ambient light. The photo-transistors provide detection signals proportional to the amount of infrared light detected, which are then summed and amplified, forming a composite signal. The amplitude of this composite signal is indicative of the thickness of the layer of fat and may be displayed and recorded.

It is therefore a principal object of the present invention to provide a device for noninvasively determining the thickness of a layer of fat.

It is a principal feature of the present invention to use infrared light to measure the thickness of fat.

The foregoing and other objectives, features and advantages of the present invention will be more readily understood upon consideration of the following detailed description of the invention taken in conjunction with the accompanying drawings.

DETAILED DESCRIPTION OF THE INVENTION

Figure 1:
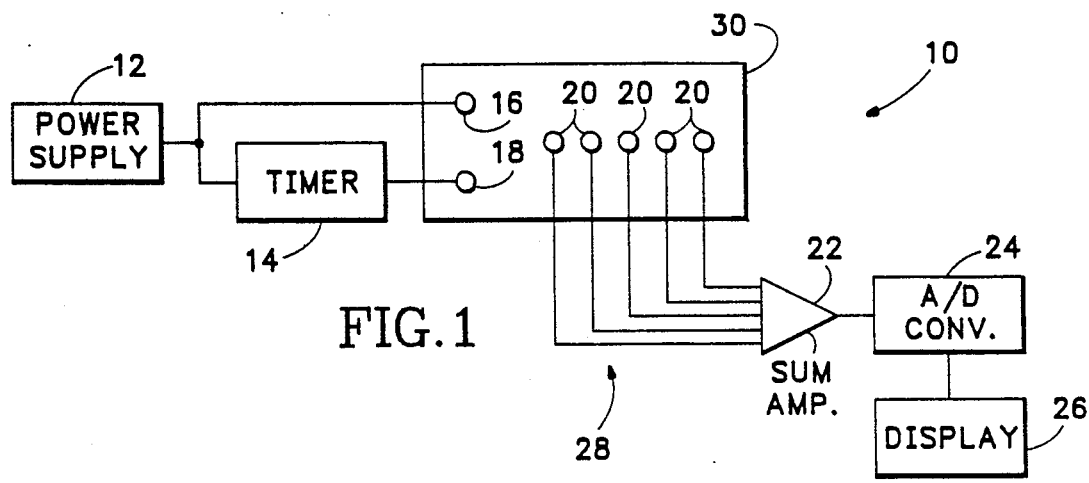
FIG. 1 is general block diagram of an illustrative embodiment of a device for measuring the thickness of a layer of fat according to the present invention.

Referring to the drawings, in FIG. 1 a block diagram is shown of a meter 10 which embodies the present invention. The meter comprises a power supply 12, two infrared emitting diodes (IREDs) 16 and 18, five photo-transistors 20, a summing amplifier 22, an analog-to-digital (A/D) converter 24, and a display 26. The IREDs and the photo-transistors constitute a sensor 28 which is enclosed on all sides except its bottom by a light shield 30. The power supply 12 biases the first IRED 16 to provide a steady, low-intensity infrared (IR) light. The timer 14 controls the second IRED 18 to provide periodic pulses of high intensity IR light.

Figure 2:
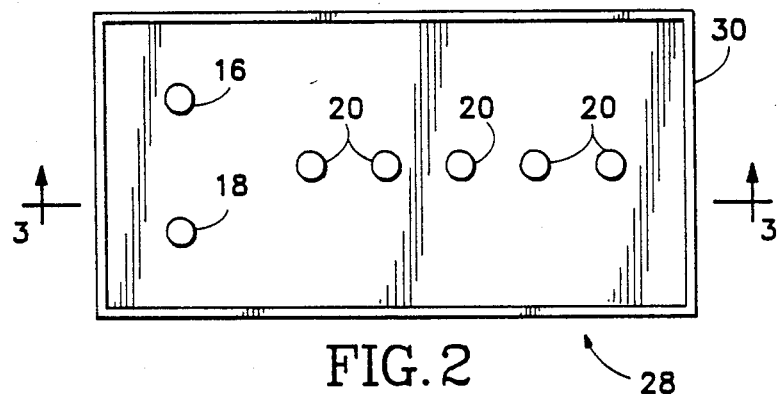
FIG. 2 is a bottom view of the sensor of the device of FIG. 1.

Referring now to FIG. 2, the two IREDs 16 and 18 are positioned adjacent each other and are equidistant from each of the five photo-transistors 20. The light shield 30 surrounds the IREDs and photo-transistors on the four sides and top while allowing their bottom surfaces to be exposed.

Figure 3:
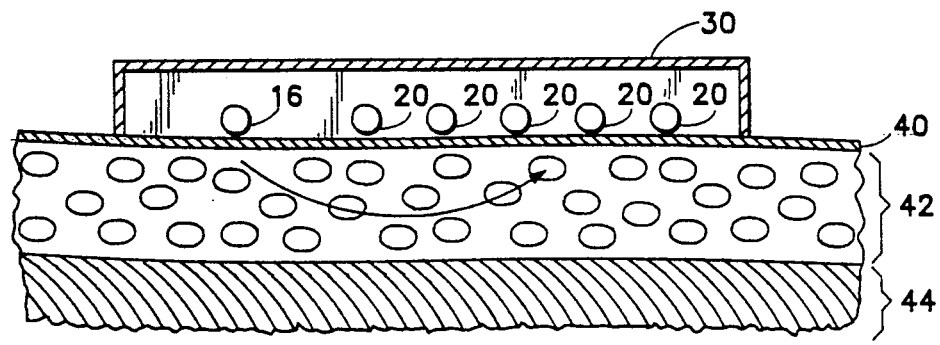
FIG. 3 is a elevational view of the sensor in contact with flesh, taken along line 3—3 of FIG. 2.

The sensor 28 is shown in contact with skin tissue 40 in FIG. 3. Beneath the skin tissue is a layer of adipose, or fat, tissue 42, beneath which is muscle tissue 44. The light shield 30 prevents the photo-transistors 20 from being exposed to ambient light. The first IRED 16 (FIG. 2) floods the adjacent volume of flesh with low intensity IR light, establishing a base illumination level and thereby reducing the effect of ambient light on the measurement. The second IRED 18 emits periodic pulses of high intensity IR light. The IR light from both IREDs is refracted by the adipose tissue; its intensity at locations distant from the IREDs being indicative of the thickness of the layer of fat 42.

Each of the photo-transistors 20 provides a detection signal representative of the intensity of IR light present at its respective location. Referring again to FIG. 1, these detection signals are combined by the summing amplifier 22, resulting in a composite signal. The A/D converter 24 converts the composite signal to digital form and supplies it to the display 26 which provides an indication of the thickness of the fat layer.

It will be appreciated by those of ordinary skill in the art that other types of infrared detectors, such as photodiodes, may be used in place of the photo-transistors described above. The larger surface area of the photodiodes may have the advantage of being less sensitive to small irregularities immediately under the skin, such as caused by vascularization.

Figure 4:
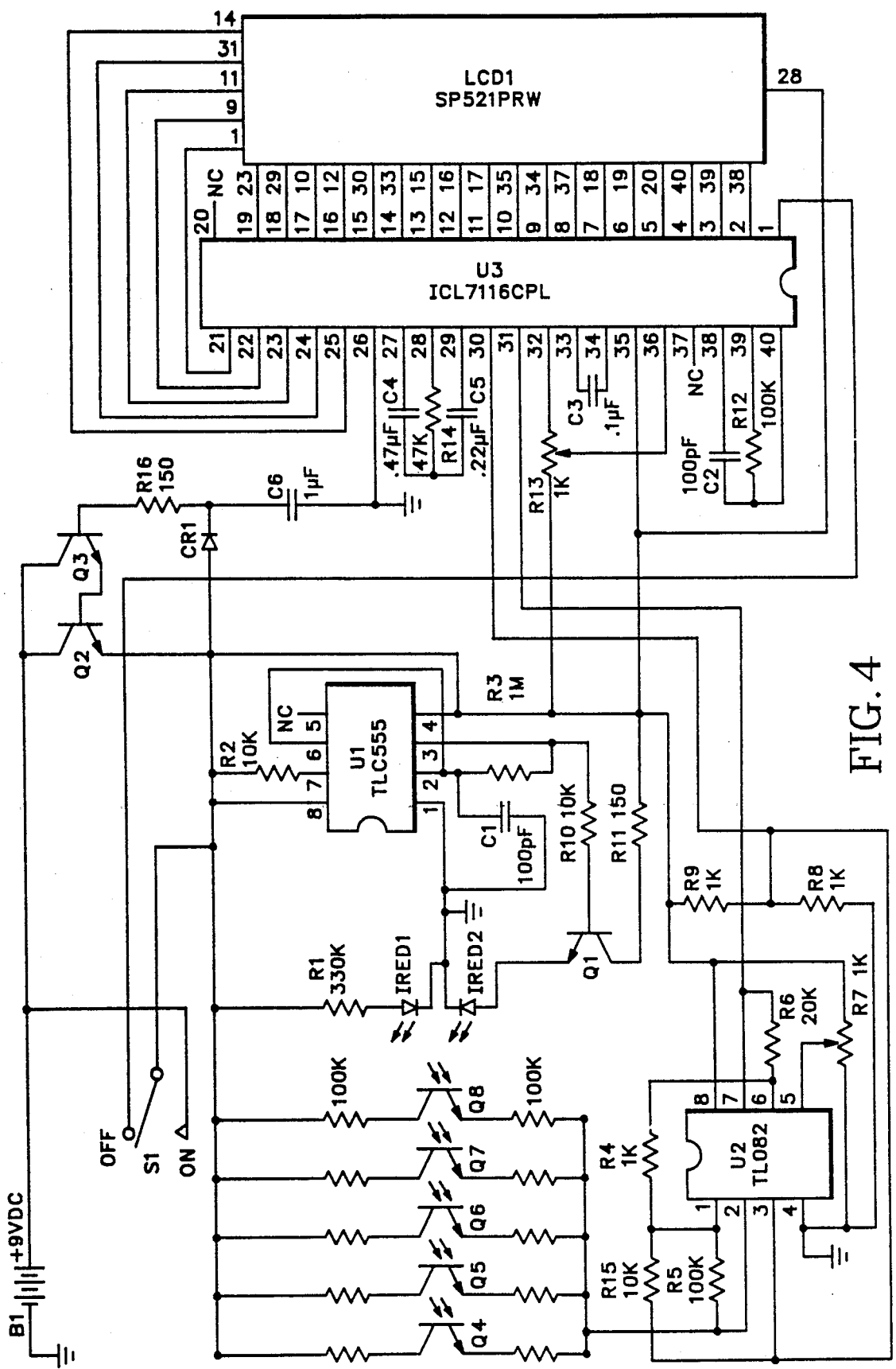
FIG. 4 is a schematic diagram of a circuit for a device which embodies the present invention.

A schematic diagram of an exemplary circuit embodying the present invention is shown in FIG. 4. Switch S1 allows the fat meter to be turned on or off by respectively connecting and disconnecting it from the battery power supply B1.

In operation, the first infrared emitting diode IRED1 is biased on, with resistor R1 limiting its intensity. The state of the second infrared emitting diode IRED2 is controlled by a transistor Q1 which, in turn, is controlled by device U1. Device U1 is a standard 555 timer configured as a 10 kHz oscillator with a 50-percent duty cycle. Resistor R11 limits the intensity of IRED2. The IR light emitted by IRED1 and IRED2 preferably has a wavelength of $950\pm20$ nanometers (nm) and a bandwidth of approximately 55 nm.

The five photo-transistors Q4-Q8 detect IR light having wavelengths within the range of 460 to 1060 nm, with maximum sensitivity at wavelengths of 850 nm, and produce respective detection signals having magnitudes corresponding to the intensities of IR light detected. These detection signals are summed by device U2, which is a commercially available, dual operational amplifier TL082. Variable resistor R7 provides a means for adjusting an offset value to compensate for the detection signals caused by the steady, low-intensity IR light from IRED1. The resulting composite signal, present on pin 7 of U2, is provided to pin 31 of device U3, a commercially available A/D converter. Resistors R9 and R8 form a voltage divider which determines a reference voltage for the A/D converter. Resistors R14 and R12 and capacitors C2-C5 have values as recommended by the manufacturer of device U3 for 10 kHz input signals. The digital output of the A/D converter U3 is updated to correspond to the analog input at pin 31 when pin 1 of U3 is open-circuited. When pin 1 is forced "high," then the digital output of U3 is held constant at the value present when pin 1 became high.

The digital output of the A/D converter U3 is provided to device LCD1, a liquid crystal display (LCD), which displays a digital representation of the digital output of the A/D converter.

When the switch S1 is moved to the ON position, capacitor C6 charges to the battery's voltage less the voltage drop across diode CR1. When the switch is returned to the OFF position, transistors Q2 and Q3 conduct, and the voltage at the emitter of transistor Q2 is approximately two base-emitter voltage drops less than the voltage across C6. Capacitor C6, prevented from discharging through diode CR1, discharges in approximately fifteen seconds through transistor Q3. During this time, transistor Q2 provides power to the balance of the circuitry.

Additionally, when switch S1 returns to the normal OFF position, pin 1 of the A/D converter is connected to the emitter of transistor Q2, causing the A/D converter to hold its digital output.

In this manner, the meter may be used to measure the thickness of a fat layer where the user cannot see the meter. The meter is placed on the skin where the fat is to be measured and the switch S1 is pressed ON momentarily. The photo-transistors Q4-Q8 measure the intensity of the IR light, providing detection signals to the summing amplifier U2. The summing amplifier provides the composite signal to the A/D converter U3 which converts it to digital form. When the switch returns to the OFF position, the digital output of the A/D converter is held. The user may then remove the meter from the skin and look at the LCD display which will continue to display the reading until capacitor C6 is discharged.

The terms and expressions which have been employed in the foregoing specification are used therein as terms of description and not of limitation, and there is no intention, in the use of such terms and expressions, of excluding equivalents of the features shown and described or portions thereof, it being recognized the scope of the invention is defined and limited only by the claims which follow.

What is claimed is:

1. A device for measuring the thickness of a layer of fat, comprising:
    (a) a first infrared emitter means for emitting infrared light at a steady intensity;
    (b) a second infrared emitter means for periodically emitting pulses of infrared light;
    (c) a plurality of infrared detector means for detecting and sensing the magnitude of infrared light emitted by said first and second emitter means after transmission of said infrared light at least partially through said layer of fat and producing respective detection signals in response thereto, said plurality of infrared detector means and said first and second infrared emitter means being arrayed substantially in a single plane;
    (d) summing means for summing said detection signals and producing a composite signal corresponding to a summation of said detection signals; and
    (e) output means responsive to said composite signal for producing an indication corresponding to said composite signal and indicative of the thickness of said layer of fat.

2. The device of claim 1 wherein said output means includes means for producing said indication in the form of a digital display.

3. The device of claim 1 wherein at least one of said plurality of infrared detector means is positioned equidistant from said first and second infrared emitter means.

4. The device of claim 1 further comprising a momentary ON switch controllingly connected with said first and second infrared emitter means so as to cause said first and second infrared emitter means to emit infrared light when said ON switch is activated, and means responsive to said ON switch for providing said indication corresponding to said composite signal for a predetermined time after said ON switch has been activated.

5. The device of claim 1 further including adjustable means for offsetting a portion of said composite signal to compensate for a portion of said composite signal resulting from sensing infrared light emitted by said first infrared emitter means.

6. A method of detecting the thickness of a layer of fat beneath a skin surface, comprising the steps of:
    (a) directing infrared light into said layer of fat continuously at a first intensity from a first location on said skin surface and simultaneously intermittently directing infrared light into said layer of fat from a nearby second location for predetermined periods of time at a second intensity which is greater than said first intensity;
    (b) detecting respective intensities of said infrared light present at said skin surface at a plurality of respective predetermined distances from said location;

(c) producing respective detection signals having respective values corresponding to said respective intensities;

(d) summing said respective detection signals to produce a composite signal having a composite value;

(e) adjusting said composite signal to compensate for portions of said detection signals which result from directing infrared light into said light of fat continuously at said first intensity; and (f) in response to said composite signal, providing an indication corresponding to said composite value and indicative of the thickness of said layer of fat.

7. A device for measuring the thickness of a layer of fat in a human body, comprising:

(a) infrared emitter means for emitting infrared light;

(b) a plurality of infrared detector means for sensing the magnitude of said infrared light and producing respective detection signals in response thereto;

(c) means for supporting said plurality of infrared detector means and said infrared emitter means arrayed substantially in a single plane with said infrared detector means arranged at predetermined distances from said infrared emitter means;

(d) summing means for summing said detection signals and producing a composite signal corresponding to a summation of said detection signals; and (e) output means responsive to said composite signal for producing an indication corresponding to said composite signal and indicative of the thickness of said layer of fat.

8. The device of claim 7 wherein said infrared light has a wavelength within the range of 930 nanometers to 970 nanometers.

* * * * *

UNITED STATES PATENT AND TRADEMARK OFFICE
CERTIFICATE OF CORRECTION

PATENT NO. : 5,014,713

DATED : May 14, 1991

INVENTOR(S) : Alan Roper et al.

It is certified that error appears in the above-identified patent and that said Letters Patent is hereby corrected as shown below:

Col. 5, line 10, Change "said light of fat" to --said layer of fat--.

Signed and Sealed this

Twenty-second Day of September, 1992

Attest:

DOUGLAS B. COMER

*Attesting Officer*  *Acting Commissioner of Patents and Trademarks*